United States Patent [19]

Takami et al.

[11] 4,417,228

[45] Nov. 22, 1983

[54] GAS COMPONENT DETECTOR

[75] Inventors: Akio Takami; Tsutomu Saito; Toshifumi Sekiya; Kazutoshi Tanaka, all of Nagoya, Japan

[73] Assignee: NGK Spark Plug Co., Ltd., Nagoya, Japan

[21] Appl. No.: 375,602

[22] Filed: May 6, 1982

[30] Foreign Application Priority Data

May 8, 1981 [JP] Japan .............................. 56-67178[U]

[51] Int. Cl.³ .............................................. H01L 7/00
[52] U.S. Cl. .................................... 338/34; 73/27 R; 422/98
[58] Field of Search .................... 338/28, 34; 73/27 R; 422/98

[56] References Cited

U.S. PATENT DOCUMENTS

| | | | |
|---|---|---|---|
| 3,901,067 | 8/1975 | Boardman, Jr. et al. | 422/98 X |
| 3,933,028 | 1/1976 | Laud et al. | 73/27 R X |
| 4,007,435 | 2/1977 | Tien | 338/28 X |
| 4,013,943 | 3/1977 | Chou et al. | 73/27 R X |

FOREIGN PATENT DOCUMENTS

| | | |
|---|---|---|
| 53-12692 | 2/1978 | Japan . |
| 54-21393 | 2/1979 | Japan . |
| 54-39087 | 3/1979 | Japan . |
| 54-134495 | 10/1979 | Japan . |
| 55-105933 | 7/1980 | Japan . |

Primary Examiner—C. L. Albritton
Attorney, Agent, or Firm—Sughrue, Mion, Zinn, Macpeak, and Seas

[57] ABSTRACT

A gas component detector having a gas component detecting element made of sintered metal oxide for indicating an electrical resistance according to the components of a gas to be detected. A pair of electrodes transmit the electrical resistance indicated by the gas component detecting element and a ceramic tube has through-holes into which said pair of electrodes are inserted. The ceramic tube has a cylindrical ceramic heater which is prepared by having a piece of wet ceramic sheet on which a print pattern is formed with metal paste for forming a heat generator wound on and bonded to the outer wall of the ceramic tube before sintering. The heater is then sintered to be integral with the ceramic tube.

6 Claims, 6 Drawing Figures

GAS COMPONENT DETECTOR

BACKGROUND OF THE INVENTION

This invention relates to a gas component detector made of metal oxide. It is used, for instance, in controlling the components of gas exhausted from an internal combustion engine to within predetermined values in order to render the gas harmless. More particularly, this invention relates to a gas component detector in which the assembly structure of a resistance variation type gas detector and a cylindrical ceramic heater is improved. Also, the labor, time and cost required for assembling and manufacturing the device are reduced, and deterioration of the dynamic response of assembled parts is prevented.

Solid electrolytic gas sensors using sheath heaters are disclosed in Japanese Patent Application Laid-Open Nos. 134495/1979 and 21393/1979 and Japanese Utility Model Application Laid-Open No. 39087/1979. A resistance variation type gas detector incorporating a cylindrical ceramic heater is disclosed in Japanese Utility Model Application No. 105933/1980 and have been proposed as gas component detectors. In such gas component detectors, a heater is employed to heat the sensor so that the characteristics of the sensor will not be adversely affected by temperature variations, especially by low temperature. This will now be described with reference to FIG. 1 which is a longitudinal sectional view of the aforementioned resistance variation type gas detector disclosed, by way of example, in Japanese Utility Model Application No. 105933/1980.

In the gas detector of FIG. 1, a gas component detecting element 1 made of sintered metal oxide, a pair of electrodes 2 for transmitting an electrical resistance indicated by the gas component detecting element 1, and a ceramic tube 3 which insulates the pair of electrodes and holds the detecting element are formed into one unit with heat-resisting cement 6. The unit is inserted into a sintered cylindrical ceramic heater 4 which is separately manufactured. The space between the ceramic tube 3 and the ceramic heater 4 is filled with heat-resisting cement 6, so that the former is bonded to the latter. The resultant assembly is then dried. The assembly includes a heat-generating wire 5 as shown in FIG. 1. The assembly is protected from damage by a metal portion 7 and a protector sheath 8 having gas discharging holes 9, in use.

In FIG. 1, reference numeral 10 designates a holding metal sleeve. In the detector thus constructed, the cylindrical ceramic heater is manufactured in addition to the ceramic tube. While manufacture of the cylindrical ceramic heater is not costly per se, the heater is strained during the sintering process. Therefore, when the ceramic tube is inserted into the cylindrical ceramic heater, the gap between the tube and the heater is not uniform. Accordingly, considerable time and labor are needed to fill the gap with heat-resisting cement, and it is difficult to completely fill the gap therewith therefore many voids are remained at the refractory cement. Thus, the resulting heater assembly has a high thermal resistance between the sensor element and the ceramic heater, then the effective heating of the sensor element cannot be realized. Furtheremore, since gas exhausted from an internal combustion engine is left in the void, the response of the detecting element deteriorates.

SUMMARY OF THE INVENTION

This invention is directed to the elimination the above-described difficulties accompanying a conventional gas component detector. A specific feature of the invention is that the ceramic tube has a cylindrical ceramic heater which is formed according to a method in which a piece of green ceramic sheet on which a print pattern is formed with metal paste for forming a heat generator is wound on and bonded to the outer wall of the ceramic tube prior to sintering process. It is then sintered to be integral with the ceramic tube.

In the gas component detector of the invention, the cost required for manufacturing its parts and the cost required for assembly, such as the cost required for cementing, is reduced to two-thirds of that of the conventional gas component detector in which the ceramic tube is bonded to the ceramic heater with heat-resisting cement. The resultant assembly is smaller in size, and therefore it can be installed even in the equipment in which only small spaces are available. Since the ceramic tube is co-fired with the ceramic heater so that there is no gap therebetween, the exhausted gas is nearly completely absent therein, and accordingly, the response of the component detecting element is excellent.

Furthermore, according to the invention, a portion of the gas component detecting element is exposed outside from one end face of the cylindrical ceramic heater in which a wiring pattern is buried. Therefore, the gas component detecting element can sufficiently contact exhausted gas, and the response thereof is improved as much. Furthermore, a difficulty exists in the prior art where, during the bonding work with heat-resisting cement, the cement is stuck to the surface of the detecting element to degrade the function of the detecting element. This problem is eliminated according to the invention. Moreover, according to the invention, a recess is formed in one end face of the ceramic tube integral with the ceramic heater, and a part of the gas component detecting element is secured to the recess with heat-resisting cement. The detector thus formed is substantially equal in response to those which are formed according to the above-described methods, and is protected from damage when handled. The above-described gas component detecting element and a temperature compensating thermistor can be readily juxtaposed. The detector thus formed has improved functionality.

Embodiments of this invention will be described with reference to the accompanying drawing and the description of the preferred embodiments that follow.

DESCRIPTION OF THE PREFERRED EMBODIMENTS

Figure 1:
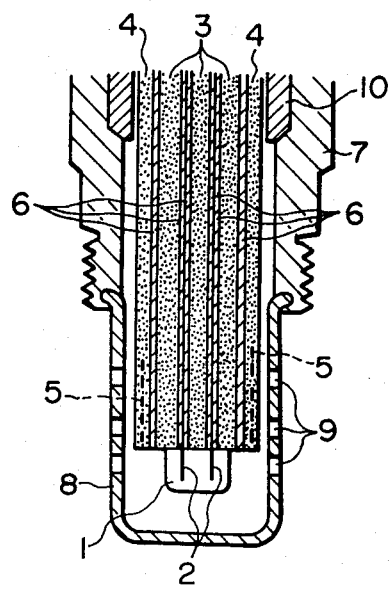
FIG. 1 is a longitudinal sectional view of a conventional gas component detector.
Figure 2:
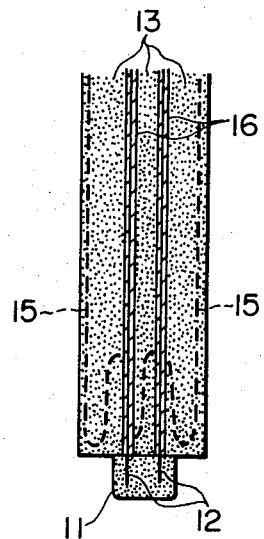
FIG. 2 is a longitudinal sectional view showing a first embodiment of this invention in which an outer metal shell is removed.

FIG. 2 is a longitudinal sectional view of a gas component detector from which a holding outer metal shell has been removed. In FIG. 2, reference numeral 11 designates a gas component detecting element. A pair of electrodes 12 for transmitting an electrical resistance which is detected by the detecting element 11, and a ceramic tube 13 which is made burried with a cylindrical ceramic heater 15 with through-holes into which the pair of electrodes are inserted are fixed with heat-resisting cement 16. A method of manufacturing the ceramic tube integral with the ceramic heater of this embodiment will now be described.

A mixture is prepared by mixing ceramic powder with a molding assistant. A ceramic tube 5.0 mm in outside diameter having through-holes is formed by extruding the mixture. The ceramic tube is cut to a 50 mm length after being dried. A piece of wet ceramic sheet 0.5 mm in thickness is cut to a size of $16 \times 45$ mm$^2$. A metallized heat-generating conductor is printed on a surface of the ceramic sheet with tungsten powder paste. A bonding agent is applied to the surface of the ceramic sheet if it is necessary. The ceramic sheet thus treated is wound on the ceramic tube with the printed surface inside, so that the ceramic sheet is fixedly bonded to the ceramic tube. Then, lead terminal connecting parts are printed at the ends of the heat-generating conductor. After being calcined for removal of resin, the ceramic tube wrapped with the ceramic sheet is sintered at 1500° C. in a non-oxidation atmosphere. Thus, the ceramic tube integral with the heater has been obtained. The lead terminal connecting parts are plated with nickel. Lead wires are brazed to the lead terminal connecting parts thus treated. The ceramic tube with the ceramic heater, which has been manufactured as described above, will be referred to as "assembly I".

Figure 3A:
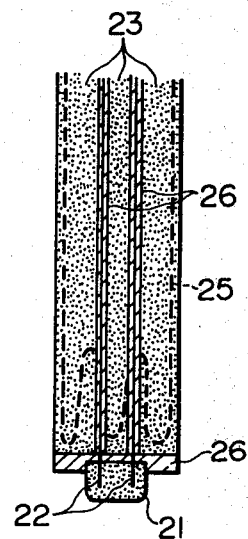
FIGS. 3A and 3B are a longitudinal sectional view and a bottom view respectively showing a second embodiment of the invention.
Figure 3B:
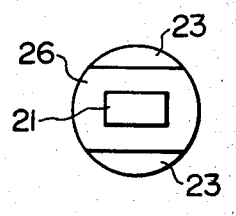

Another assembly is formed in the same manner as the assembly I, and a recess for receiving the sensor element is formed in one end face of the assembly thus formed. This assembly will be referred to as "assembly II". FIG. 2 and FIG. 3A are sectional views of assemblies I and II coupled to the gas component detecting elements (not covered by the outer metal shells), respectively. FIG. 3B is a top view of the assembly II with the gas component detecting element. In FIG. 3, reference numeral 21 designates the gas component detecting element and element 22 defines electrodes fixed with heat-resisting cement 26 which fixes the lower part of the detecting element. Element 23 is the ceramic tube with the ceramic heater, and element 25, the heater.

Figure 4A:
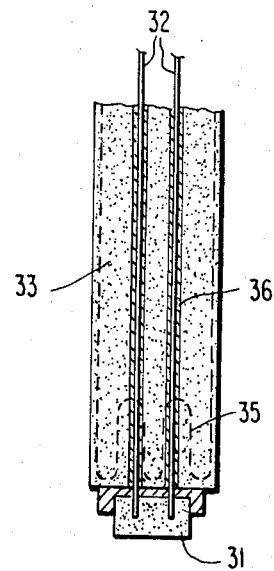
FIGS. 4A and 4B are elongitudinal sectional view and a bottom view respectively showing a modification of the second embodiment of this invention where the gas component, detecting element and the temperature compensating thermistor are juxtaposed.
Figure 4B:
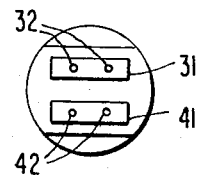

Instead of the ceramic tube in the first embodiment, a ceramic tube with four holes is employed in a second embodiment. The gas component detecting element and a temperature compensating thermistor are juxtaposed. FIG. 4A is a longitudinal sectional view of this embodiment in which the gas detecting component element and the temperature compensating thermistor are juxtaposed. FIG. 4B is an end view of FIG. 4A. In FIG. 4A and FIG. 4B, reference numeral 33 designates a ceramic tube having four through-holes with a ceramic heater 35. Element 31 designates the gas component detecting element, 32 designates a pair of electrodes thereof which are fixed in the holes with a temperature-resisting cement 36 and 41 designates a temperature compensating thermistor element with a pair of electrodes 42 fixed in the holes by a heat-resisting cement. The detector thus manufactured is improved than that in the first embodiment.

It is apparent that modifications of this invention will be apparent to one skilled in the art without departing from the scope thereof.

What is claimed is:

1. In a gas component detector having: a gas component detecting element made of sintered metal oxide with a varying electrical resistance according to the components of a gas to be detected; a pair of electrodes for transmitting the electrical resistance of said gas component detecting element; and a ceramic tube having through-holes into which said pair of electrodes are inserted, the improvement comprising a method of making said ceramic tube with a cylindrical ceramic heater comprising the steps of; forming on a green ceramic sheet a print pattern with metal paste for forming a heat generator; winding and bonding said sheet to the outer wall of said ceramic tube before sintering; and co-fired to integrate said heater with said ceramic tube.

2. A gas component detector comprising:
a gas component detecting element made of sintered metal oxide with a varying electrical resistance according to the components of a gas to be detected;
a pair of electrodes for transmitting the electrical resistance of said gas component detecting element;
a ceramic tube having through-holes into which said pair of electrodes are inserted; and
a cylindrical ceramic heater integral with said ceramic tube and comprising a green ceramic sheet having printed thereon a pattern for heat generator defined by a metal paste, said sheet wound on and bonded to the outer wall of said ceramic tube prior to sintering followed by sintering of said tube having said sheet wound around it to integrate said heater with said ceramic tube.

3. A gas component detector as in claim 2, comprising a portion of said gas component detecting element exposed form one end face of said cylindrical ceramic heater, and wherein a wiring pattern defined by said print pattern is buried in said sintered ceramic.

4. A gas component detector as in claim 2, wherein said ceramic tube integral with said cylindrical ceramic heater has a recess in one end face thereof, and a portion of said gas component detecting element is fixedly secured to said recess with heat-resisting cement.

5. A gas component detector as in claims 2, 3, or 4, wherein said electrodes protrudes through an end face of said cylindrical ceramic heater into said gas component detecting element.

6. A gas component detector as in claim 2, further comprising a temperature compensating thermistor in an end of said ceramic tube integral with said cylindrical ceramic heater.

* * * * *